(12) United States Patent
Yanagisawa et al.

(10) Patent No.: US 6,992,312 B2
(45) Date of Patent: *Jan. 31, 2006

(54) MEDICAL CHARGED PARTICLE IRRADIATION APPARATUS

(75) Inventors: Masaki Yanagisawa, Tokyo (JP);
Hiroshi Akiyama, Hitachiohta (JP);
Kohei Kato, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/815,808

(22) Filed: Apr. 2, 2004

(65) Prior Publication Data

US 2004/0183034 A1    Sep. 23, 2004

Related U.S. Application Data

(62) Division of application No. 10/253,586, filed on Sep. 25, 2002.

(30) Foreign Application Priority Data

Feb. 28, 2002 (JP) .............................. 2002-052708

(51) Int. Cl.
*A61N 5/00* (2006.01)
(52) U.S. Cl. ...................... 250/492.3; 378/17; 378/65; 600/1
(58) Field of Classification Search ............. 250/492.1, 250/492.3, 505.1, 398, 493.1, 497.1; 378/150, 378/152, 165, 17, 65; 600/423; 601/20, 601/1; 607/88
See application file for complete search history.

(56) References Cited

U.S. PATENT DOCUMENTS 4,455,489 A * 6/1984 Brown ....................... 250/398
5,751,002 A * 5/1998 Ogata et al. ........... 250/492.21

(Continued)

FOREIGN PATENT DOCUMENTS

JP    5-192419    8/1993

OTHER PUBLICATIONS

Steven D. Chang et al., Robotics and Radiosurgery—The Cyberknife, Department of Neurosurgery, Stereotactic and Functional Neurosurgery, 2001, p. 204-208, Stanford University School of Medicine, Stanford, CA.

(Continued)

*Primary Examiner*—John R. Lee
*Assistant Examiner*—David A. Vanore
(74) *Attorney, Agent, or Firm*—Dickstein Shapiro Morin & Oshinsky LLP

(57) ABSTRACT

A medical charged particle irradiation apparatus capable of irradiation from upward and horizontal directions and performing a preparing/ascertaining work without any separate device such as a moving capsule or the like comprising a patient's bed, on which a patient lies, a transport equipment for injecting and transporting charged particle beams toward the patient's bed, an irradiation field forming device for forming an irradiation field for the beams transported by the transport equipment, and a gantry provided to be rotatable about an axis of rotation, and wherein the irradiation field forming device is eccentrically arranged such that an axis of irradiation passes a position different from the axis of rotation, and the patient's bed is arranged on an opposite side of the transport equipment to a plane, which contains the axis of rotation and is substantially perpendicular to the axis of irradiation.

3 Claims, 5 Drawing Sheets

U.S. PATENT DOCUMENTS 5,818,058 A * 10/1998 Nakanishi et al. ....... 250/492.3
5,969,367 A * 10/1999 Hiramoto et al. ........ 250/492.3
5,993,373 A * 11/1999 Nonaka et al. ................. 600/1
6,218,675 B1 * 4/2001 Akiyama et al. ........ 250/492.3
6,316,776 B1 * 11/2001 Hiramoto et al. ........ 250/492.3
6,803,591 B2 * 10/2004 Muramatsu et al. ..... 250/492.3
2003/0163015 A1 * 8/2003 Yanagisawa et al. .......... 600/1

OTHER PUBLICATIONS

John R. Adler, Jr. MD et al., Image-guided Robotic Radiosurgery, Neurosurgery, Jun. 1999, p. 1299-1307, vol. 44, No. 6.

* cited by examiner

AT THE TIME OF VERTICAL IRRADIATION

AT THE TIME OF HORIZONTAL IRRADIATION

MEDICAL CHARGED PARTICLE IRRADIATION APPARATUS

CROSS REFERENCE TO RELATED APPLICATION

The present application is a divisional application of U.S. patent application Ser. No. 10/253,586, filed on Sep. 25, 2002, the disclosure of which is incorporated by reference herein.

BACKGROUND OF THE INVENTION

1. Field of the Invention

The invention relates to a medical charged particle irradiation apparatus for using charged particles to treat cancer, lump and so on.

2. Description of the Related Art

A medical charged particle irradiation apparatus for irradiating charged particles such as proton, carbon ion, or the like on an affected part of a patient to treat cancer, lump and so on injects charged particles, which are generated in an ion source and accelerated by a synchrotron or the like, to guide the same to an irradiation field forming means containing a collimator or the like, and irradiates the charged particles on a patient lying below the irradiation field forming means after an irradiation field conformed to a configuration of the affected part is formed in the irradiation field forming means.

At this time, a patient ordinarily lies on a patient's bed with the face upward, and it is necessary to perform irradiation from an appropriate angular position (for example, from upward or from substantially horizontally, or the like) in accordance with position and state of the affected part. Also, exposure dose from various directions is suppressed while irradiation is made on the affected part from a plurality of directions (multiple-field), whereby there is produced an effect that a predetermined exposure dose on the affected part can be achieved depending upon a weight of the part and exposure dose on other portions than the affected part can be lowered to reduce unnecessary exposure.

For example, Japanese Patent Laid-Open No. 192419/1993 describes a rotary irradiation therapeutic device as a prior art taking account of the above. This device comprises a substantially cylindrical-shaped rotary frame, an outer periphery of which is rotatably supported by rollers, and which mounts therein transport means (deflecting device and vacuum duct), irradiation field forming means (beam adjusting device), and an irradiation chamber provided with a patient's bed (irradiation bed). The transport means injects charged particle beams at a diametrically central portion of the rotary frame to transport the same to the irradiation field forming means while swinging up the same toward a diametrically outer periphery. The irradiation field forming means is arranged on a diameter passing an axis of rotation of the rotary frame to cause beams to be injected diametrically inwardly of the rotary frame from a distal end of the transport means arranged on the outer periphery of the rotary frame and to form an irradiation field for the beams to cause the beams to be injected into the irradiation chamber. The irradiation chamber is rotatably (turnably on its axis) arranged (in other words, rotatable about an axis of rotation of the rotary frame) on a beam emission side position of the irradiation field forming means in the rotary frame to constantly maintain the patient's bed substantially horizontal irrespective of a rotating position of the rotary frame.

With such construction, in the case where it is desirable to irradiate beams from, for example, above the affected part in accordance with position and state of the affected part, the rotary frame is turned to position the transport means on an upper side and the irradiation chamber on a lower side to cause beams having been swung up substantially vertically upward from the diametrically central portion of the rotary frame to be passed downward to be irradiated on the patient's bed in the irradiation chamber disposed below the irradiation field forming means from above. Also in the case where it is desirable to irradiate beams from, for example, laterally (horizontal direction) of the affected part, the rotary frame is turned to position the transport means on one lateral side (for example, lefthand) and the irradiation chamber on the other lateral side (for example, righthand) to cause beams having been swung up leftward from the diametrically central portion of the rotary frame to be passed horizontally from lefthand to righthand to be horizontally irradiated on the patient's bed in the irradiation chamber disposed rightwardly of the irradiation field forming means.

However, the above prior art involves the following problems.

That is, the prior art provides a construction, in which the rotary frame provided with the irradiation chamber capable of turning on its axis is turned in order to irradiate beams from above and in a horizontal direction in accordance with a position of the affected part or the like as described above. As a result, a heightwise position of the patient's bed is considerably varied as the irradiation chamber makes a circular motion (vertical movement) due to turning of the rotary frame. Concretely, since a rotating irradiation body provided with the transport means and the irradiation field forming means has a turning diameter of, for example, around 5 m, a distance, over which the patient's bed rises from a lowest position for irradiation from above to a lateral position for irradiation from horizontal irradiation, amounts to about 2.5 m corresponding to a radius of rotation.

With the above prior art, a moving capsule capable of following the positional variation of the patient's bed is separately provided in juxtaposition to one sense of an axial direction of the rotary frame to cope with the situation, and a physician (or a technician) performing the irradiation preparing/ascertaining work can get on the moving capsule to easily reach a position of the patient's bed for improvement in convenience. However, because of the need of providing such moving mechanism as the moving capsule separate from the rotary frame, the entire device becomes large in size (in particular, in the axial direction of the rotary frame) and the mechanism is made complex.

SUMMARY OF THE INVENTION

An object of the invention is to provide a medical charged particle irradiation apparatus capable of irradiation from upward and horizontal directions and performing a preparing/ascertaining work without the provision of any separate moving mechanism such as a moving capsule or the like.

(1) In order to attain the above object, the invention provides a medical charged particle irradiation apparatus for irradiating charged particles on an affected part of a patient, comprising a patient's bed, on which a patient lies, a transport equipment for injecting and transporting charged particle beams toward the patient's bed, an irradiation field forming means for forming an irradiation field for the beams transported by the transport equipment, and a rotating irradiation body provided to be rotatable about an axis of rotation, and wherein the irradiation field forming means is eccentrically arranged such that an axis of irradiation thereof passes a position different from the axis of rotation, and the patient's bed is arranged on an opposite side of the transport equipment to a plane, which contains the axis of rotation and is substantially perpendicular to the axis of irradiation.

In the case where it is desirable to enable irradiation from above to laterally (a substantially horizontal direction) in a state, in which a patient lies with the face upward, an irradiation device capable of varying a direction of irradiation from upward to either of right and left senses in a substantially horizontal direction (in other words, variable in the range of, for example, 90°) relative to an affected part will do provided that irradiation is performed with a head and feet reversed when a patient lies.

In consideration in the variable range of 90°, with the above prior art, the patient's bed is in a lowest position at the time of upward irradiation and in a lateral position at the time of horizontal irradiation where the rotating irradiation body is turned 90° with the result that a distance, over which the patient's bed rises from the lowest position to the lateral position amounts to, for example, about 2.5 m substantially corresponding to a radius of the rotating irradiation body.

In contrast, according to the invention, the axis of irradiation of the irradiation field forming means is made eccentric so as to pass a different position from the center of rotation (in other words, the axis of irradiation involves a predetermined angle so as not to intersect the center of rotation), whereby a position of the patient's bed at the time of upward irradiation is not a lowest position as in the above prior art but can rise an amount, which correspond to the above eccentricity, somewhat to a position in either direction laterally of the lowest position. Also, a position of the patient's bed at the time of horizontal irradiation can be correspondingly made a position somewhat lower than the other lateral position unlike the lateral position (the other lateral position in accordance with the above) in the above prior art. That is, the patient's bed 8 when the rotating irradiation body is turned to displace the patient's bed from a position at the time of upward irradiation to a position at the time of horizontal irradiation moves from the position at the time of upward irradiation→gradually descends to a lowest position→gradually ascends to a position at the time of horizontal irradiation. In this manner, since the position of the patient's bed at the time of upward irradiation and the position of the patient's bed at the time of horizontal irradiation are not a lowest position but can be made a position somewhat higher than the lowest position, variation (in other words, difference of height between the lowest position and the position at the time of upward irradiation or the position at the time of horizontal irradiation) of a heightwise position of the patient's bed in displacements, that is, the position at the time of upward irradiation→the lowest position→the position at the time of horizontal irradiation can consequently be suppressed considerably.

Meanwhile, in the rotating irradiation body, the transport equipment having charged particle beams injected at, for example, a diametrically center (axis of rotation of the rotating irradiation body) once directs (swings up) the beams to a diametrically outer peripheral side, then transports the beams a predetermined distance in the axial direction of rotating irradiation body, and again directs the beams to the diametrically inner peripheral side of rotating irradiation body at a distal end to inject the beams into the irradiation field forming means. A plurality of deflecting electromagnets for directing (deviating) the beams are provided on the beam transport path.

With such construction, in the case where the patient's bed is arranged at the center of rotation of the rotating irradiation body, and the irradiation field forming means is arranged on the diametrically outer peripheral side thereof, a distal end of the transport equipment is positioned near the diametrically outer peripheral side thereof than the irradiation field forming means in order to inject beams into the irradiation field forming means. As a result, the transport means is shaped to be considerably enlarged toward the diametrically outer peripheral side of the rotating irradiation body, so that the rotating irradiation body is increased in diameter of rotation.

Hereupon, according to the invention, the patient's bed is arranged on an opposite side of the transport means to the axis of rotation, more specifically, on an opposite side of the transport means to a plane, which contains the axis of rotation and is substantially perpendicular to the axis of irradiation. Thereby, the irradiation field forming means can also be made offset an amount, by which the patient's bed is offset toward the opposite side of the transport means, toward the opposite side of the transport means, with the result that the above enlargement toward the diametrically outer peripheral side thereof can be reduced. As a result, the rotating irradiation body can be reduced by such amount in diameter of rotation.

As described above, according to the invention, the above action of reducing the rotating irradiation body in diameter of rotation is added to the action of suppressing heightwise variation in a position of the patient's bed between the position at the time of upward irradiation and the position at the time of horizontal irradiation, whereby their multiplied effect can suppress heightwise variation of the patient's bed (difference of height) to, for example, around 1.5 m at maximum through suitable setting of positions of respective parts such as eccentric dimension or the like. Thereby, even in a state, in which the patient's bed is in the highest position (for example, the position at the time of upward irradiation or the position at the time of horizontal irradiation), a physician or a technician can perform an irradiation preparing/ascertaining work or the like while standing on a floor without the use of any specific device, so that convenience can be considerably improved. Also, since the heightwise position of the patient's bed is suppressed, a patient can be enhanced in safety.

(2) In the above paragraph (1), the patient's bed is preferably rotatably suspended and supported by the irradiation field forming means.

Thereby, the patient's bed can be maintained horizontal by suitably turning the patient's bed in accordance with a rotating position of the rotating irradiation body. Also, there is produced an effect that the relative positional accuracy between a target point of an affected part and an actual irradiation point at the time of irradiation can be maintained high.

(3) In the above paragraph (2), a heavy object is more preferably provided on the patient's bed to maintain a posture thereof substantially horizontal.

Thereby, since a center of gravity of the patient's bed can be made lower than a position of suspension, the bed can be easily maintained horizontal. Also, the bed is made heavy whereby it is possible to fulfill the function of a counter weight for the transport means with respect to the axis of rotation of the rotating irradiation body.

(4) In the above paragraph (2), there are more preferably provided bed driving means for driving the patient's bed, which is rotatably suspended from and supported, to change its inclination, inclination detecting means for detecting inclination of the patient's bed, and inclination controlling means for controlling the bed driving means in accordance with results of the detecting means.

Thereby, it becomes possible to forcedly and surely maintain the bed horizontal or at a predetermined angle.

(5) In the above paragraph (1), there are more preferably provided a rotating shaft member fixed to the rotating irradiation body, a central axis of which shaft member constitutes the axis of rotation, and support means for rotatably supporting the rotating shaft member.

With a construction, in which the axis of rotation of the rotating irradiation body is constituted by the rotating shaft member, it is possible to considerably decrease deformation, such as flexure or the like, due to a weight of large-sized heavy elements such as the transport means, the irradiation field forming means, or the like, as compared with the case where such large-sized heavy elements are supported by a substantially cylindrical-shaped rotary frame provided with no shaft. Thereby, it is possible to prevent that degradation in relative positional accuracy between the target point and the irradiation point, which is attributable to the flexure or the like and to achieve improvement in accuracy of irradiation. Also, the construction provided with a shaft enables a shaft member to support load of all the elements of the rotating irradiation body whereby a diametrical dimension of the rotating irradiation body can be decreased as compared with the case of supporting by means of the substantially cylindrical-shaped rotary frame provided with no shaft.

(6) In the above paragraph (5), there are more preferably provided rotating drive means for rotatingly driving the rotating shaft member, rotation detecting means for detecting a position of rotation of the rotating shaft member, and rotation controlling means for controlling the rotating drive means in accordance with results of the detecting means.

DESCRIPTION OF THE PREFERRED EMBODIMENTS

An embodiment of the invention will be described below with reference to the drawings.

Figure 2:
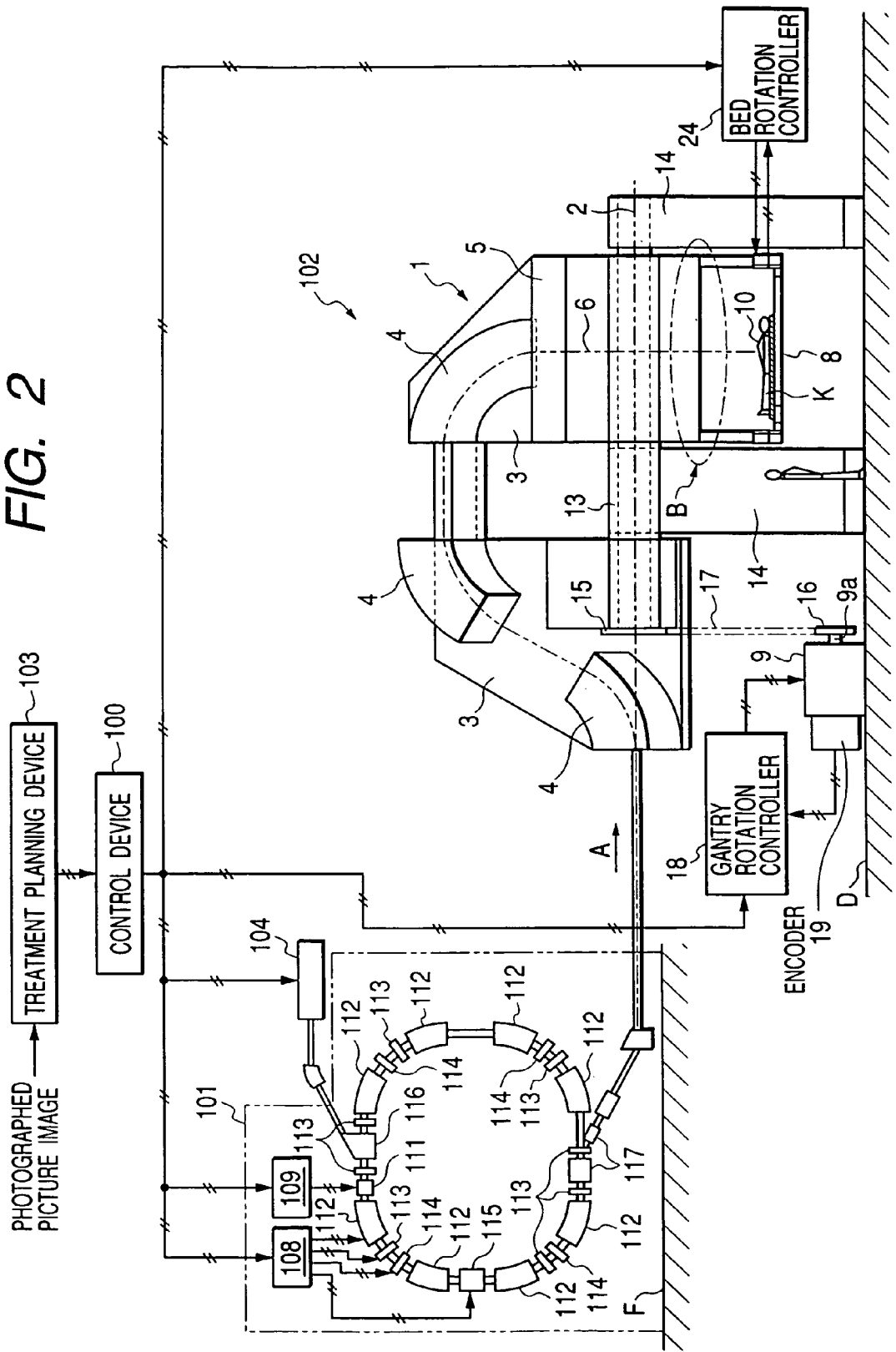
FIG. 2 is a conceptional view showing an entire constitution of a charged particle irradiation therapeutic system provided with the medical charged particle irradiation apparatus of FIG. 1.

FIG. 2 is a conceptional view showing an entire constitution of a charged particle irradiation therapeutic system provided with a medical charged particle irradiation apparatus according to an embodiment.

In FIG. 2, with the irradiation therapeutic system, charged particle beams (referred below to as beams) having been accelerated by a charged particle generating device (=acceleration device; in this example, a synchrotron but may be other acceleration devices such as cyclotron or the like) 101 in accordance with a treatment plan mapped out in a treatment planning device 103 and under the control of a control device 100 are output by an irradiation device 102 to be irradiated on an affected part of a patient K. The irradiation device 102 rotates about an axis of rotation (described later) to be able to irradiate beams on the affected part from a plurality of directions.

(1) Construction of a Synchrotron 101

The synchrotron 101 comprises a high-frequency applying device 111 for increasing a betatron oscillation amplitude of beams through application of high-frequency magnetic field and electric field (referred below to as high-frequency electromagnetic field) to beams, deflecting electromagnets 112 for bending orbits of beams, four-pole electromagnets 113 for controlling betatron oscillation of beams, six-pole electromagnets 114 for exciting resonance at the time of beam emission, a high-frequency accelerating cavity 115 for giving energy, that is, accelerating beams, an injector 116 for injecting beams into the synchrotron 101, and emission deflectors 117 for emitting beams from the synchrotron 101.

When the control device 100 issues an emission command to a preaccelerator 104, the preaccelerator 104 correspondingly emits beams of low energy, which beams are conducted to the injector 116 of the synchrotron 101 via a beam conveying system to thereby be injected into the synchrotron 101. The injected beams are bent in path by the deflecting electromagnets 112 to go around within the synchrotron 101. At this time, beams go around within the synchrotron 101 while being caused the four-pole electromagnets 113 to make betatron oscillation, the number of which is suitably controlled by quantity of excitation of the four-pole electromagnets 113 whereby beams go around stably within the synchrotron 101. The high-frequency accelerating cavity 115 applies a high-frequency electric field to beams in the course of going-around whereby energy is given to beams to accelerate the beams, so that energy is increased.

When energy of beams going around within the synchrotron 101 is increased to a predetermined energy E, application of energy to beams by the high-frequency accelerating cavity 115 is stopped, beams are varied in orbital gradient under the known control with the four-pole electromagnets 113, the six-pole electromagnets 114 and the high-frequency applying device 111 to cause resonance to rapidly increase the betatron oscillation amplitude, and the emission deflectors 117 cause the synchrotron 101 to emit beams.

In the above operation of the synchrotron 101, the control device 100 determines energy E of beams irradiated on the affected part along predetermined directions of irradiation (irradiated in a plurality of directions) on the basis of a depth of the affected part input from the treatment planning device (described in detail later) 103. Also, patterns of values of current fed to each of the deflecting electromagnets 112, the four-pole electromagnets 113, and the high-frequency accelerating cavity 115 and required for accelerating beams to energy E in the synchrotron 101, and values of current fed to the high-frequency applying device 111 and the six-pole electromagnets 114 and required for emitting beams of energy E are calculated. The respective values of current as calculated correspond to energy E every device to be stored in a storage means in the control device 100 to be output to a power source 108 or a power source 109 at the time of acceleration and at the time of emission.

(2) Construction of an Irradiation Device 102

An essential part of the invention relates to an irradiation device 102. Details of the device will be sequentially described.

Figure 1:
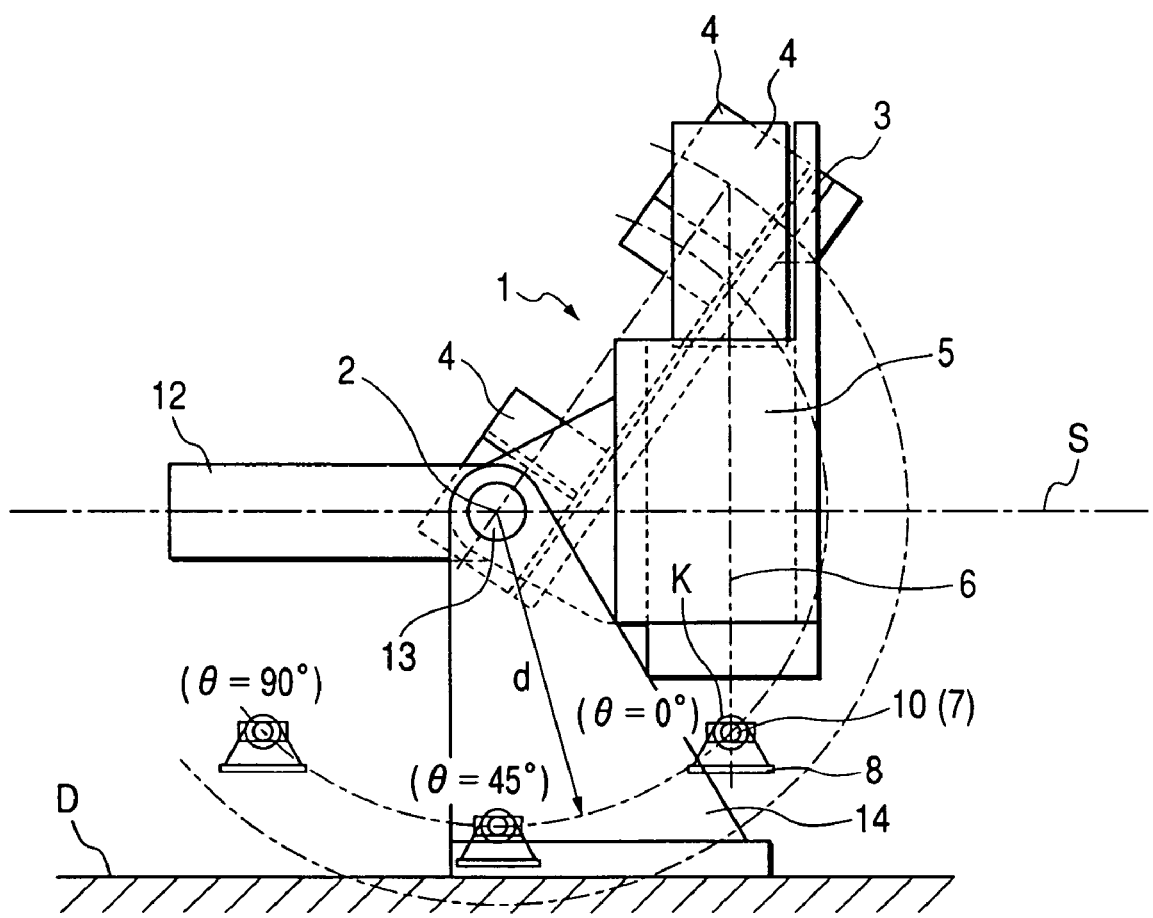
FIG. 1 is a front view showing an entire schematic construction of a medical charged particle irradiation apparatus according to an embodiment of the invention.

FIG. 1 is a front view showing an entire schematic construction of the irradiation device 102 (however, a motor 9 for rotary driving of a gantry described later and its peripheral construction are omitted from the figure). In FIGS. 1 and 2, the irradiation device 102 comprises a gantry (rotary irradiation body) 1 provided with a transport equipment 4, an irradiation field forming device 5 and a rotating support structure 3, a rotating rod 13, which is fixed to the gantry 1 and whose central axis defines a center 2 of rotation (axis of rotation) of the gantry 1, a patient's bed 8 turnably suspended from and supported on the irradiation field forming device 5, a support frame 14 for rotatably supporting the rotating rod 13, and a gantry rotating drive motor 9 for generating a rotating drive force for the rotating rod 13.

The transport equipment 4 provided on the gantry 1 comprises, for example, deflecting electromagnets, four-pole electromagnets or the like (all these are omitted from the figure), and permits beams emitted from the synchrotron 101 to be injected coaxially of the center 2 of rotation (axis of rotation) of the gantry 1. The injected beams are first bent in orbit by the deflecting electromagnets to be transported to a side of the irradiation field forming device 5 with the betatron oscillation adjusted by the four-pole electromagnets.

Also, the irradiation field forming device 5 comprises, for example, scanning electromagnets, a scattering body, a ridge filter, a bolus, collimator, or the like (all these are omitted from the figure) to form an irradiation field so that intensity and configuration of beams assume values set by the treatment planning device 103. That is, beams conducted into the irradiation field forming device 5 first pass between magnetic poles of the scanning electromagnets to be deflected in a manner to provide for circular scanning in a position of the affected part, and then are scattered by the scattering body to be enlarged in diameter, after which the ridge filter gives energy of beams a distribution conformed to a thickness of the affected part. Thereafter, beams are input into the bolus to generate an energy distribution conformed to a lower configuration of the affected part, and further formed into a horizontal configuration of the affected part to be irradiated on the affected part.

At this time, according to a feature of the invention, the irradiation field forming device 5 is arranged eccentrically (substantially vertically in a reference position of rotation (a state shown in FIG. 1) described later) such that its axis of irradiation (axis of irradiation) 6 passes a different position from the center 2 of rotation of the gantry 1 (in other words, does not pass the center 2 of rotation). Also, the transport equipment 4 when being in the reference position of rotation correspondingly swings beams incident from the synchrotron 101 upwardly obliquely toward a radially outer periphery, then transports the beams in an axial direction of the gantry 1, and directs the beams substantially vertically downward at a distal end to make the beams incident upon the irradiation field forming device 5. In addition, a counter weight 12 intended for adjustment of weight balance is fixed on a side of the rotating rod 13 opposite to the gantry 1.

The transport equipment 4 and the irradiation field forming device 5 are mounted on the rotating support structure 3 fixed to the rotating rod 13 (alternatively, the rod 13 may be fixed to the support frame 14 and the rotating support structure 3 may be supported to be rotatable about the rotating rod 13). Thereby, the gantry 1 composed of the rotating rod 13, the rotating support structure 3, the transport equipment 4 and the irradiation field forming device 5 are unitary together to be rotatable about the center 2 of rotation.

With the irradiation device 102 in the embodiment, the gantry 1 constructed to be rotatable about the center 2 of rotation can turn from a vertical irradiation position (=reference position, in other words, a position where an axis of the counter weight 12 forms an angle $\theta=0°$ relative to the horizontal, see FIG. 3A described later) where the axis of irradiation 6 in the irradiation field forming device 5 as shown in FIG. 1 becomes vertical, to a horizontal irradiation position (see FIG. 3B described later, in other words, a position where $\theta=90°$) where the gantry 1 is turned 90° clockwise as viewed in FIG. 1 to make the axis of irradiation 6 horizontal). Thereby, it is possible to perform irradiation in a direction in the range from irradiation on a patient K lying on the patient's bed 8 from vertically upward (corresponding to $\theta=0°$ in FIG. 3A), to irradiation from one sense of a right and left direction (righthand in the example in FIG. 1, FIG. 3B). At this time, since irradiation in a direction in the range from irradiation on a patient K lying on the patient's bed 8 from vertically upward, to irradiation from the other sense of the right and left direction (lefthand in FIG. 1) is made possible by having a patient K lying on the patient's bed 8 with a head and feet reversed, the above positions are combined to enable irradiation on a patient K from all directions (vertical irradiation to horizontal irradiation in the right and left direction) in the range of 180°.

In addition, with the present embodiment, the reference position of rotation of $\theta=0°$ is set such that as shown in FIG. 1, a height from an installation surface D to the patient's bed 8 is minimum at a position of $\theta=45°$ and maximum at positions of $\theta=0°$ and $\theta=90°$ (the positions are at the same level). In addition, it goes without saying that a patient K gets on and off the patient's bed 8 in the position ($\theta=45°$) where the height of the patient's bed 8 is minimum.

Figure 4:
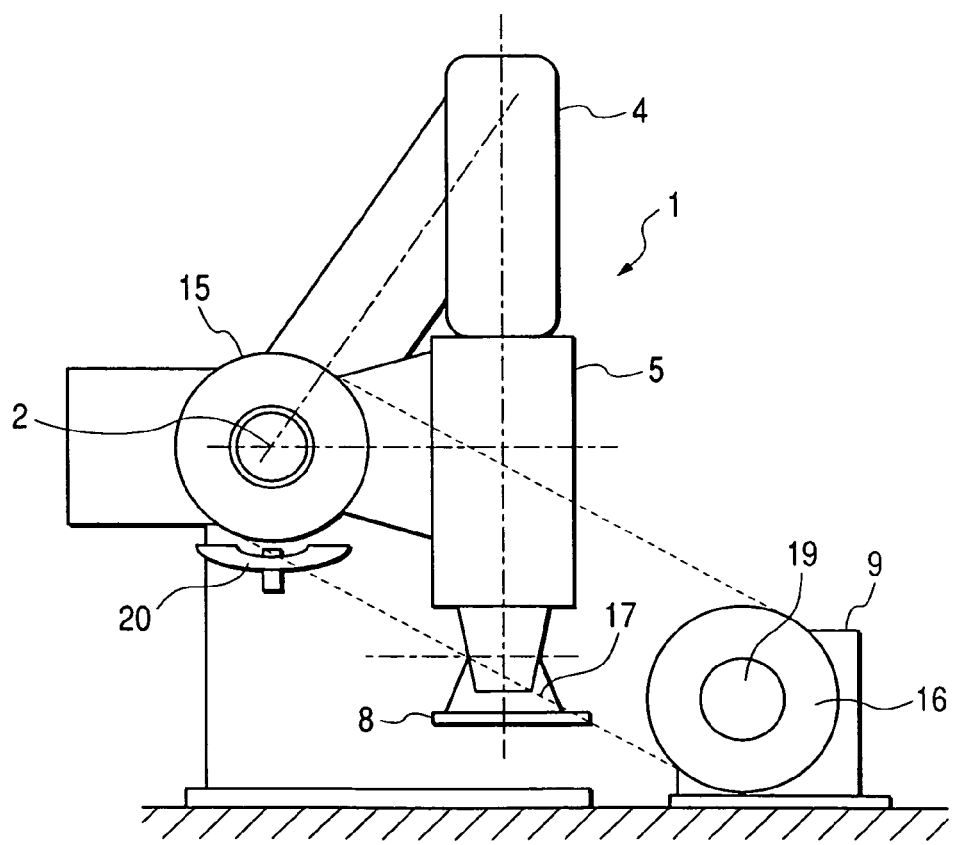
FIG. 4 is a view showing a detailed constitution related to rotating driving of a gantry and an essential part of the constitution shown in FIG. 1.

FIG. 4 is a view showing a detailed constitution related to rotating driving of the gantry 1 and an essential part of the constitution shown in FIG. 1. In FIG. 4, a drive force can be transmitted to the rotating rod 13 by connectingly providing, for example, a chain 17 or the like between a pulley 15 fixed on a shaft end of the rotating rod 13 and a pulley 16 provided on a one shaft end (lefthand in FIG. 2) of a rotating shaft 9a of the gantry rotating drive motor 9 and circulatingly driving the chain 17.

The gantry rotating drive motor 9 is, for example, a known servomotor to be driven by a drive command signal output from a gantry rotation controller 18 on the basis of a control signal from the control device 100. At this time, arranged on the other shaft end (lefthand in FIG. 2) of the rotating shaft 9a of the gantry rotating drive motor 9 and made coaxially integral with a motor part is a rotary encoder 19 to output to the gantry rotation controller 18 a pulse signal (in other words, a detection signal of the rotating speed of the rotating shaft 9a) every a certain minute rotating angle.

When a direction of irradiation on the affected part of a patient K from the gantry 1 is to be set or modified, a control signal conformed to the direction of irradiation is output to the gantry rotation controller 18 from the control device 100. The gantry rotation controller 18 feedback controls the gantry rotating drive motor 9 on the basis of a control signal from the control device 100 and a detection signal from the rotary encoder 19 so that the gantry 1 comes to a predetermined angular position. Thereby, the gantry 1 is rotatingly driven to the above-mentioned set angular position to be moved to a position where beams can be irradiated on a patient from the above-mentioned direction of irradiation.

In addition, a known inclinometer may be provided somewhere on the gantry 1 or the counter weight 12 to input its detection signal into the gantry rotation controller 18 to feedback control the gantry rotating drive motor 9 on the basis of the detection signal and a control signal from the control device 100. In any events, when coming to a predetermined angular position, the gantry 1 is preferably stopped in the turning position by, for example, a rotation braking brake 20 provided on an outer periphery of the pulley 15.

In addition, a rotating drive source for the gantry 1 is not limited to an electric type one such as the gantry rotating drive motor 9 but can make use of hydraulic pressure, air pressure or the like, and a drive force transmitting system for the gantry can make use of rack and pinion, drive with a plurality of gears, belt, spring mechanism or the like other than the above pulley system. Detection of angular positions is not limited to an encoder but known angle meters may be used.

Meanwhile, the patient's bed 8 is constructed to be able to be rotatingly driven so that the patient's bed 8 even when being in any position can be maintained horizontal relative to the gantry 1, which can assume various rotating positions about the center 2 of rotation in the manner described above (alternatively, the patient's bed 8 can be inclined at a predetermined angle relative to the axis of irradiation 6).

Figure 5:
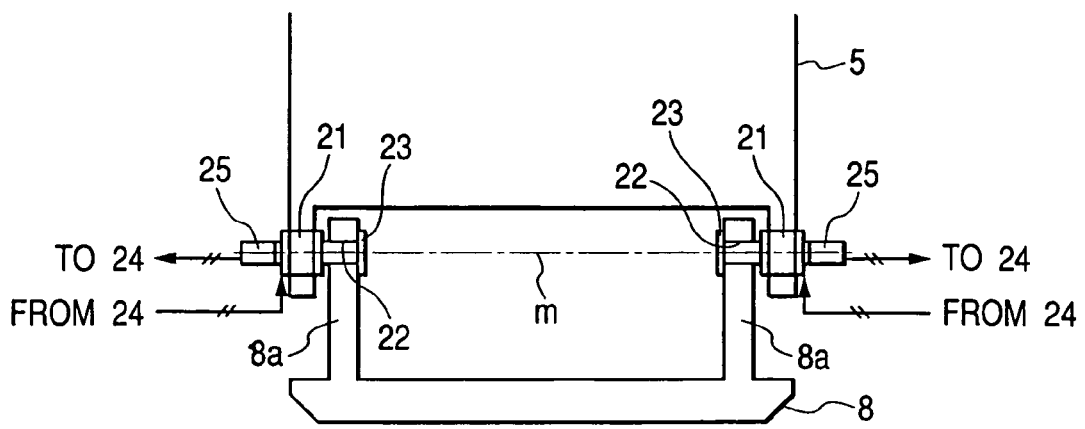
FIG. 5 is an enlarged view of a B part shown in FIG. 2, representative of a detailed support construction for a patient's bed.

FIG. 5 is an enlarged view of a B part in FIG. 2, representative of a detailed support construction for the patient's bed 8. In FIG. 5, bed rotating drive motors 21, 21 (mounted in two locations in a longitudinal direction of the patient's bed 8) are provided to be coaxial with an axis m of rotation of the patient's bed 8 in a lower end of the irradiation field forming device 5. Shaft ends on one sides (centrally in a right and left direction in FIG. 5) of rotating shafts 21a of the bed rotating drive motors 21 are inserted into through holes 22 provided on bracket portions 8a of the patient's bed 8 and fixed to the bracket portions 8a by means of stopper members 23, whereby drive force of the gantry rotating drive motor 9 is transmitted to turn the patient's bed 8 to enable changing a relative rotating angle (in other words, an inclination), which the patient's bed 8 forms relative to the irradiation field forming device 5.

The bed rotating drive motors 21 are, for example, known servomotors like the above-mentioned gantry rotating drive motor 9 as shown in FIG. 2, and driven by a drive command signal output from a bed rotation controller 24 on the basis of a control signal from the control device 100.

At this time, arranged on the other shaft ends (both end sides in a right and left direction in FIG. 5) of the rotating shafts 21a of the bed rotating drive motors are rotary encoder units 19 to be made coaxially integral with the motor parts and to output to the bed rotation controller 24 a pulse signal (a detection signal of the rotating speed of the rotating shafts 21a) every a certain minute rotating angle.

When the posture of a patient K is to be set or modified upon setting or modification of a direction of irradiation on the affected part of a patient K from the gantry 1, a control signal conformed to the direction of irradiation is output to the bed rotation controller 24 from the control device 100. The bed rotation controller 24 feedback controls the bed rotating drive motors 21 on the basis of a control signal from the control device 100 and a detection signal from the encoder units 25 so that the patient's bed 8 comes to a predetermined angular position relative to the irradiation field forming device 5. Thereby, the patient's bed 8 is rotatingly driven to the above-mentioned set angular position to be modified in posture to a position where beams from the gantry 1 can be irradiated on the affected part from a predetermined direction of irradiation.

In addition, a known inclinometer may be provided somewhere on the patient's bed 8 to input its detection signal into the bed rotation controller 24 to feedback control the bed rotating drive motors 21 on the basis of the detection signal and a control signal from the control device 100. In any events, when coming to a predetermined relative angular position, the above feedback control is preferably continued taking account of the shift of center of gravity caused by a subtle change in posture of a patient K as far as a patient K is loaded on the patient's bed 8. Also, with a view to performing irradiation of higher quality, a triaxial moving mechanism and a triaxial rotating mechanism may be provided on the patient's bed 8.

In addition, a rotating drive source for the patient's bed 8 is not limited to an electric type one such as the bed rotating drive motors 21 but can make use of hydraulic pressure, air pressure or the like, and a drive force transmitting system can make use of rack and pinion, drive with a plurality of gears, belt, spring mechanism or the like other than the above direct coupling system. Detection of angular positions is not limited to an encoder but known angle meters may be used.

Figure 3A:
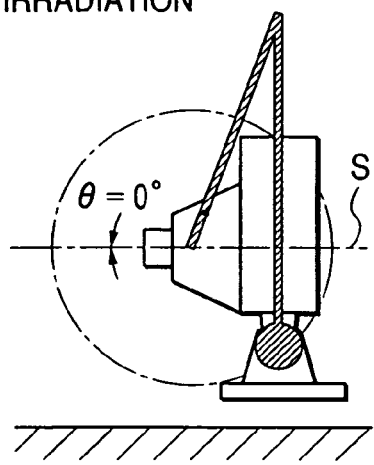
FIG. 3A is a view illustrating a state, in which vertical irradiation is performed.
Figure 3B:
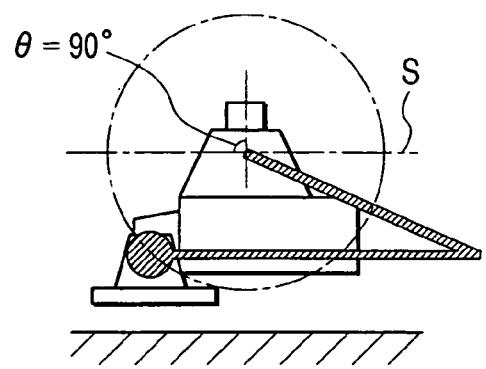
FIG. 3B is a view illustrating a state, in which horizontal irradiation is performed.

In addition, according to a feature of the invention, even when the gantry 1 is in any position (in the range of from θ=0° to 90°) in the direction of rotation and the patient's bed 8 itself is in any position relative to the irradiation field forming device 5 in the direction of rotation, the patient's bed 8 is arranged on a side opposite to the transport equipment 4 with respect to a plane S, which contains the above described center 2 of rotation and is substantially perpendicular to the axis of irradiation 6 (see FIG. 1 and FIGS. 3A and 3B).

Figure 6A:
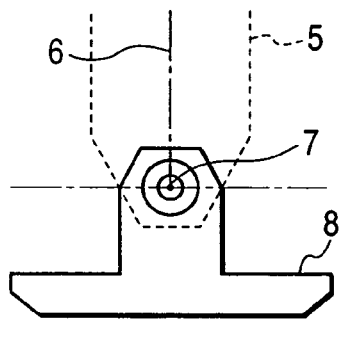
FIG. 6A is a view illustrating a construction near a connection between a patient's bed and an irradiation field forming apparatus at the time of vertical irradiation.
Figure 6B:
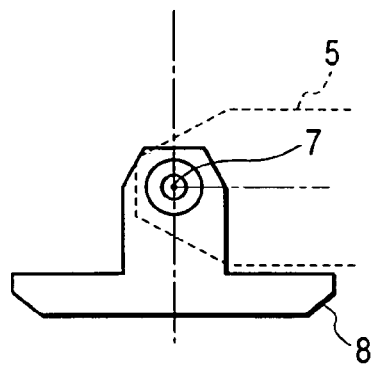
FIG. 6B is a construction drawing representative of the construction near the connection between the patient's bed and the irradiation field forming apparatus at the time of horizontal irradiation.

Also, at this time, the patient's bed 8 and the irradiation field forming device 5 are preferably constructed in such a manner that the axis m of rotation of the patient's bed 8 corresponds to an actual irradiation point 7 of beams as shown in FIGS. 6A and 6B even at the time of vertical irradiation (a state shown in FIG. 6A; corresponding to FIG. 3A) and at the time of horizontal irradiation (a state shown in FIG. 6B; corresponding to FIG. 3B).

Further, it is desired that a X-ray receptor be installed on an extension of the axis of irradiation 6 beyond the patient's bed 8 to constantly face the axis of irradiation 6 at front ways. Also, it is desired that laser markers for positioning be installed in the vicinity of a patient.

(3) Therapeutic Procedure by the Charged Particle Irradiation Therapeutic System An explanation will be given below in detail to the therapeutic procedure by means of the charged particle irradiation therapeutic system constructed in the above manner and to action of the irradiation device 102.

The treatment planning device 103 is composed of, for example, a computer, a plurality of displays, input device and patient's data base (the patient's data base may be separate from the device and connected thereto via a network), and has the function of assisting a treatment planning work performed by a physician as a step prior to an actual irradiation. Here, the treatment planning work concretely includes identification of the affected part, determination of irradiated region and irradiating direction, determination of dose of radiation to a patient, calculation of dose distribution in a patient's body, and so on.

(a) Identification of the Affected Part

For example, at the time of diagnosis prior to treatment, three-dimensional picture image data for lump inside the body are beforehand acquired by the X-ray CT examination and MRI examination. These data are numbered every patient to be preserved and managed as digital data in the patient data base. Additionally, recorded and managed in the patient data base are all data required for treatment of a patient and composed of information such as a patient's name, a patient's number, age, body height, body weight, record of medical examination and inspection, clinical history, therapeutic history, therapeutic data, and so on. A physician can suitably make access to the patient data base to acquire picture image data of the above-mentioned affected part to represent the same on a display device of the treatment planning device 103, and so can represent the picture image data of the affected part as a three-dimensional picture image as viewed from any direction or a cross sectional picture image obtained by slicing the picture image data every depth in any direction. Also, there is provided the function of assisting identification of the affected part through emphasizing contrast for each picture image, painting out a region with a certain gradation as a threshold, and the like. A physician identifies a region of the affected part while making use of these assisting functions.

(b) Temporary Selection of Irradiated Region and Irradiating Direction

Subsequently, a physician operates to determine an irradiated region, which envelopes the affected part and allows a suitable margin taking account of the possibility that the affected part is moved in the body due to respiration or the like. Further, a physician selects several (plural) irradiating directions (for example, in the range of from θ=0° to 90°) clear of internal organs, such as backbone, of high sensitivity to radioactive rays.

(c) Determination of Irradiation Filed Profile

An irradiation field picture image as viewed from an irradiation direction is displayed on the basis of several selected irradiation directions, and an irradiation filed profile covering an entire lump is emphatically displayed. Also, a three-dimensional picture image is displayed, and a position of a maximum cross section and a three-dimensional configuration following the cross section are displayed. These picture images are displayed separately in a plurality of displays in the display device. At this time, data of the three-dimensional configuration following the maximum cross section or the irradiation filed profile constitutes fundamental data (original data) for an irradiation filed, which is reshaped by the irradiation field forming device 5, or correction of irradiation.

(d) Final Determination of Irradiation Direction, Dose of Radiation, and the Like Based on information of the irradiation filed profile, the treatment planning device 103 displays positions of respective leaf plates of the collimator in the irradiation field forming device and a picture image of a maximum cross section of the irradiation filed in layers. At this time, a physician determines positions of the leaf plates on the basis of the layered picture images, and the result as determined is promptly reflected on the display of the display device. Thereafter, based on information of positional setting of the leaf plates, the treatment planning device 103 simulates a radiation dose distribution in the body through calculation to display a result of the calculated radiation dose distribution on the display device. At this time, irradiation parameters such as radiation dose, radiation energy, or the like are given by a physician, the simulation is implemented with respect to several irradiation directions selected previously, and that irradiation direction, for which the most preferable result is obtained, is finally selected by a physician.

In addition, information of setting of the selected irradiation directions, information of set positions of the leaf plates of the collimator based thereon, data of irradiation correcting tools, and irradiation parameters are preserved as therapeutic data peculiar to a patient in the patient data base.

(e) Rotating Driving of the Gantry and the Patient's Bed

The control device 100 comprises an input device and a display device as interfaces operated by a user, and can acquire treatment data of a patient including information of setting of irradiation directions determined by the treatment planning device 103, through network connection from the patient data base subordinating to the treatment planning device 103 and display the same on the display device to have the same ascertained by a physician.

At the time of actual irradiation, the control device 100 outputs, based on the above information of setting of irradiation directions, commands of starting rotation of the gantry 1 and the patient's bed 8 to the gantry rotation controller 18 and the bed rotation controller 24 aiming at a target point 10 of the affected part (see FIGS. 1 and 2) positioned on the axis of irradiation 6 and serving as an irradiation target point for implementation of irradiation and responding to input of beginning of irradiation treatment from, for example, a physician or a radiological technician engaged in assisting a physician's treatment on the basis of the above treatment plan.

The gantry rotation controller 18 serves to output a necessary control command to the gantry rotating drive motor 9, which constitutes a low-order mechanism, in accordance with a command from the control device 100, and feedback controls, upon receipt of the rotation starting command from the control device 100, the gantry rotating drive motor 9 in the manner described above to turn the gantry 1 about the rotating rod 13 (more specifically, on the center 2 of rotation) to move the same to a predetermined position of the set direction of rotation (set angle). At this time, assuming that a spacing between an actual irradiation point 7 and the center 2 of rotation is d for the target point 10 of rotation, the irradiation point 7 moves in the range of from θ=0° to 90° drawing an arc of a radius d about the center 2 of rotation (see FIG. 1).

Likewise, the bed rotation controller 24 serves to output a necessary control command to the bed rotating drive motors 21, which constitutes a low-order mechanism, in accordance with a command from the control device 100, and feedback controls, upon receipt of the rotation starting command from the control device 100, the bed rotating drive motors 21 in the manner described above to turn the patient's bed 8 relative to the irradiation field forming device 5 to maintain the patient's bed 8 in a horizontal state (alternatively, the patient's bed is set at a predetermined inclination).

In addition, in the above procedure, information of present position of and drive state of the gantry 1 controlled by the gantry rotation controller 18, and information of present position of and drive state of the patient's bed 8 controlled by the bed rotation controller 24 are transmitted to the control device 100 at all times to be displayed on the above display device of the control device 100.

In addition, the transport equipment 4 constitutes a transport means for injecting and transporting charged particle beams toward the patient's bed, the irradiation field forming device 5 constitutes an irradiation field forming means for forming an irradiation field of beams transported by the transport equipment, the rotating rod 13 constitutes a rotating shaft member, which is fixed to a rotating irradiation body and a central axis of which constitutes an axis of rotation, and the support frame 14 constitutes a support means for rotatably supporting the rotating shaft member.

Also, the gantry rotating drive motor 9 constitutes a rotating drive means for rotatingly driving the rotating shaft member, the rotary encoder 19 constitutes a rotation detecting means for detecting a rotating position of the rotating shaft member, and the gantry rotation controller 18 constitutes a rotation controlling means for controlling the rotating drive means in accordance with the detected result.

Further, the bed rotating drive motors 21 constitutes a bed driving means for driving the patient's bed, which is rotatably suspended and supported, and changing an inclination of the bed, the encoder units 25 constitutes an inclination detecting means for detecting an inclination of the patient s bed, and the bed rotation controller 24 constitutes an inclination controlling means for controlling the bed driving means in accordance with the detected result.

(5) Effect of the Embodiment

The medical charged particle irradiation apparatus according to the embodiment, provided in the charged particle irradiation therapeutic system gives the following effect.

(5-1) Capability of Upward and Horizontal Irradiation while Suppressing a Patient's Height For example, with the above-mentioned construction of the prior art, in which a rotary frame provided with an irradiation chamber capable of turning on its axis is rotated, a position of a patient's bed in a heightwise direction is much varied with a circular motion (vertical motion) of the irradiation chamber caused by rotation of the rotary frame. That is, since a diameter of rotation of an irradiation body provided with a transport means and an irradiation field forming means is around, for example, 5 m, a lift distance from a lowest position of the patient's bed for upward irradiation to a lateral position of the patient's bed for horizontal irradiation in the heightwise direction amounts to about 2.5 m corresponding substantially to a radius of rotation.

In contrast, with the irradiation device 102 according to the embodiment, the axis of irradiation 6 of the irradiation field forming device 5 is made eccentric to pass a different position from the center 2 of rotation of the gantry 1 (in other words, the axis of irradiation 6 involves a predetermined angle so as not to intersect the center 2 of rotation), whereby a position of the patient's bed 8 at the time of upward irradiation (corresponding to the position of θ=0°) is not a lowest position as in the above prior art but can rise somewhat to a position (a righthand position in FIG. 1) in either direction laterally of a lowest position (corresponding to the position of θ=45° in the embodiment). Also, a position of the patient's bed (corresponding to the position of θ=90° in the embodiment) at the time of horizontal irradiation can be correspondingly made a position somewhat lowered from the other lateral position unlike the lateral position (the other lateral position in accordance with the above) in the above prior art.

That is, the patient's bed 8 when the gantry 1 is turned to displace the patient's bed from a position (θ=0°) at the time of upward irradiation to a position (θ=90°) at the time of horizontal irradiation moves from the position (θ=0°) at the time of upward irradiation→gradually descends to a lowest position (θ=45°)→gradually ascends to a position (θ=90°) at the time of horizontal irradiation. In this manner, since the position (θ=0°) of the patient's bed 8 at the time of upward irradiation and the position (θ=90°) of the patient's bed 8 at the time of horizontal irradiation are not a lowest position but can be made a position somewhat higher than the lowest position, variation (in other words, difference of height between the lowest position (θ=45°) and the position (θ=0°) at the time of upward irradiation or the position (θ=90°) at the time of horizontal irradiation) in a heightwise position of the patient's bed in displacements, that is, the position at the time of upward irradiation→the lowest position→the position at the time of horizontal irradiation can consequently be suppressed considerably.

Figure 7:
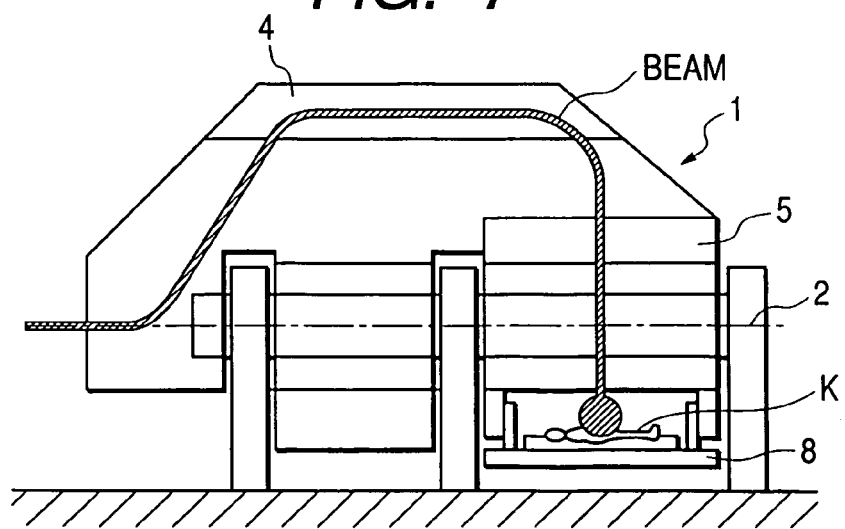
FIG. 7 is a conceptional view showing a path of beams in the gantry.

Meanwhile, in the gantry 1, the transport equipment 4 having charged particle beams injected at the center 2 of rotation of the gantry 1 once directs (swings up) the beams to a diametrically outer peripheral side as conceptionally shown in FIG. 7, then transports the beams a predetermined distance in the axial direction of the gantry 1, and again directs the beams to the diametrically inner peripheral side of the gantry 1 at a distal end to inject the beams into the irradiation field forming device 5. The plurality of deflecting electromagnets for directing (deviating) the beams are provided on the beam transport path as described above. With such construction, in the case where the transport equipment 4 is provided in a substantially cylindrical-shaped rotary frame rotatably supported, the patient's bed 8 is arranged at the center 2 of rotation of the gantry, and the irradiation field forming device is arranged on the diametrically outer peripheral side thereof as in the above prior art, a distal end of the transport equipment 4 is positioned, as conceptionally shown in FIG. 8A, near the diametrically outer peripheral side thereof than the irradiation field forming device 5 in order to inject beams into the irradiation field forming device 5. As a result, the transport equipment 4 is shaped to be considerably enlarged toward the outer peripheral side of the gantry 1, so that the gantry 1 is increased in diameter of rotation.

Figure 8A:
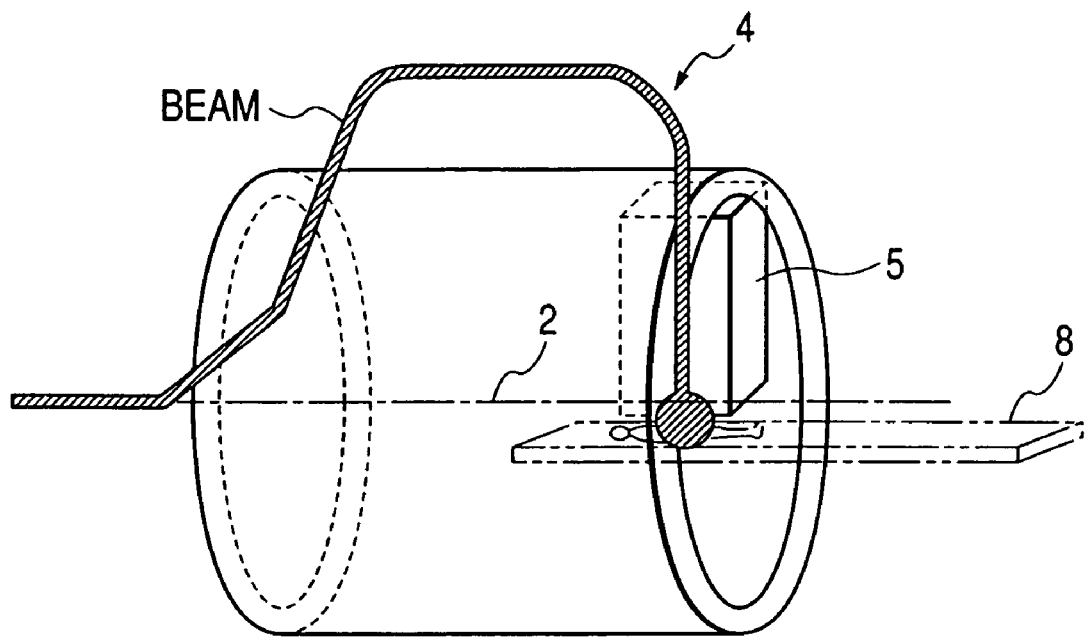
FIG. 8A is a conceptional view showing a comparative example, in which a patient's bed is arranged in a position of an axis of rotation of a gantry in a rotary frame.
Figure 8B:
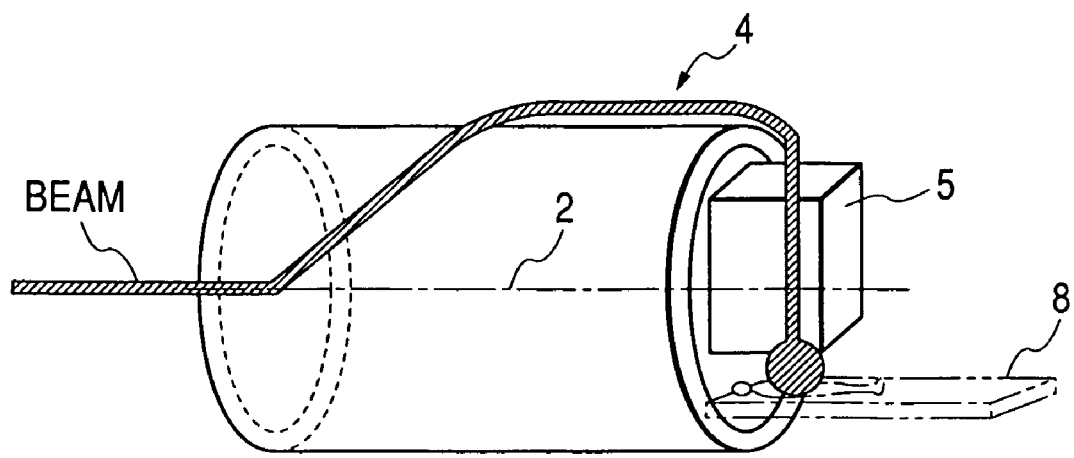
FIG. 8B is a conceptional view showing a comparative example, in which an axis of irradiation passes an axis of rotation of a gantry.

Meanwhile, in the case where the axis of irradiation 6 passes through the rotating shaft of the gantry and the patient's bed 8 is arranged nearer the diametrically outer peripheral side thereof (an opposite side of the transport equipment 4) than a position of the center 2 of rotation of the gantry in the rotating frame as conceptionally shown in FIG. 8B, the irradiation field forming device 5 can also be made offset an amount, by which the patient's bed 8 is offset toward the opposite side of the transport equipment 4, toward the opposite side of the transport equipment 4 (a lower side in FIG. 8B), as understood in comparison with FIG. 8A, with the result that the above enlargement toward the outer peripheral side thereof in the diametrical direction can be reduced. As a result, the gantry 1 can be reduced by such amount in diameter of rotation as shown in FIG. 8B.

Also, in the embodiment, the same effect as in comparative example shown in FIG. 8B can be obtained since the patient's bed 8 is arranged nearer the opposite side of the transport equipment 4 than the position of the center 2 of rotation, more specifically, on the opposite side of the transport equipment 4 (a lower side in FIG. 8B) with respect to the plane, which contains the above center 2 of rotation and is substantially perpendicular to the axis of irradiation 6.

As described above, according to the embodiment, the above action of reducing the gantry 1 in diameter of rotation is added to the action of suppressing heightwise variation in a position of the patient's bed 8 between the position ($\theta=0°$) at the time of upward irradiation and the position ($\theta=90°$) at the time of horizontal irradiation, whereby their multiplied effect can suppress heightwise variation of the patient's bed 8 (difference of height from the position $\theta=45°$ to the position $\theta=0°$ or $90°$) to around 1.5 m at maximum through suitable setting of positions of respective parts such as eccentric dimension of the axis of irradiation 6 or the like. Thereby, even in a state, in which the patient's bed 8 is in the highest position (the position $\theta=0°$ at the time of upward irradiation and the position $\theta=90°$ at the time of horizontal irradiation), a physician or a technician can perform the irradiation preparing/ascertaining work or the like while standing on a floor without any specific separate device, so that convenience can be considerably improved. Also, since the heightwise position of the patient's bed 8 is suppressed, a patient can be enhanced in safety.

(5-2) Improvement in Accuracy of Irradiation or the Like

In the case of that construction, in which respective constituent elements of the gantry 1 are arranged in, for example, the substantially cylindrical-shaped rotary frame as illustrated in the above paragraph (5-1) with reference to FIG. 8A, large-sized and heavy articles such as the transport equipment 4, the irradiation field forming device 5 or the like are supported by the substantially cylindrical-shaped rotary frame provided with no shaft. Therefore, it is difficult to suppress generation of that deformation, such as flexure or the like, in the rotary frame, which is caused by their weights, and consequently it is difficult to prevent that degradation in relative positional accuracy between the target point 10 of rotation and the irradiation point 7, which is attributable to the flexure or the like.

In contrast, with the irradiation device 102 according to the embodiment, the construction with a shaft, in which the respective constituent elements of the gantry 1 are fixed to the above rotating rod 13, can reduce generation of flexure or the like in comparison with the above construction, in which load is born by the rotary frame. Thereby, degradation in relative positional accuracy between the target point 10 and the irradiation point 7 can be prevented and irradiation accuracy can be improved.

The construction with a shaft, in which load of all the members of the gantry 1 can be supported by the rotating rod 13, can take effect in reducing the diametrical dimension of the gantry 1 as compared with the case of supporting by means of the substantially cylindrical-shaped rotary frame provided with no shaft, shown in FIG. 8A.

(5-3) Miniaturization of a Building

As described in the above paragraph (5-1), according to the embodiment, the charged particle irradiation apparatus 102 can be reduced in size as a whole since the diameter of rotation (in other words, a diametrical dimension) and axial dimension of the gantry 1 can be reduced. Thereby, for example, in the case where the synchrotron 101 is installed on an ordinary floor surface F with its beam injecting axis corresponding to the center 2 of rotation of the gantry 1, it is not required that a level of the installation surface D, on which the irradiation apparatus 102 is installed, be so much lower than the floor surface F, and a semi-underground construction will do. Accordingly, while for example, the constitution shown in FIG. 8A requires a three-floor construction or so as a building for receiving the synchrotron 101 and the irradiation apparatus 102, the entire building can be considerably reduced in dimension (in particular, heightwise dimension).

(5-4) Lightening of the Irradiation Apparatus

The construction, in which the irradiation field forming device 5 is made offset and enlargement of the transport equipment 4 is correspondingly reduced as described in the above paragraph (5-1), makes it possible to make the position of gravity of the entire irradiation apparatus 102, which is provided with the transport equipment 4 and the irradiation field forming device 5, close to the center 2 of rotation as compared with the constitution shown in, for example, FIG. 8A. Thereby, the necessity of the counter weight 12 required for balancing of weight is decreased, and so lightening of the irradiation apparatus 102 can be achieved correspondingly.

(5-5) Others

① Utilization of Unused Space

With the irradiation device 102 in the embodiment, a large space is ensured above a patient K in the position $\theta=90°$ at the time of horizontal irradiation (see FIGS. 1 and 3B), so that a X-ray CT examination apparatus or the like is installed in this position to perform CT photographing without having a patient K getting of f the patient's bed 8. In addition, as measures of utilizing this space, a device for charging and setting equipments, such as bolus, collimator, or the like, which are provided on the irradiation field forming device 5 and must be exchanged or set every patient, can be mounted in the above position.

② No Weight Limit for the Bed

In the case of that construction, in which respective constituent elements of the gantry 1 are arranged in, for example, the substantially cylindrical-shaped rotary frame shown in, for example, FIG. 8A, as described in the above paragraph (5-2), it is desirable to make the patient's bed 8 as lightweight as possible in terms of suppressing degradation in accuracy of irradiation. In contrast, with the irradiation device 102 in the embodiment, it is possible to fulfill the duties as a counter weight for the transport equipment 4 and the irradiation field forming device 5, so that a heavy load is not problematic and therefore there is no weight limit.

In addition, the above embodiment uses the drive force of the gantry rotating drive motor 9 to forcedly rotatingly drive the patient's bed 8 in order to maintain the patient's bed 8 in a horizontal state irrespective of, for example, a rotating position of the gantry 1 ($\theta=0°$ to $90°$), but is not limited thereto. That is, the patient's bed 8 may be freely rotatably suspended from and supported by a lower end of the irradiation field forming device 5, and a heavy object (weight or the like) may be provided on the patient's bed 8 to have its weight naturally maintaining the patient's bed 8 in a horizontal posture. Also, it goes without saying that the patient's bed 8 be manufactured from a heavy material to be made a heavy object. In these cases, the function as a counter weight for the transport equipment 4 and so on as described in the above ② is further increased.

Also, according to the above embodiment, the rotating angle of the gantry 1 is in the range of from θ=0° to 90° but is not limited thereto. That is, a little wider range, for example, θ=0° to 120°, can be adopted by suitably setting the positional relationship between the center 2 of rotation of the irradiation device 102 and the irradiation point 7. Also, on the contrary, a range narrower than 90° can be adopted, in which case, for example, horizontal irradiation and irradiation in a direction close thereto suffice to be made by inclining the patient's bed 8 a little angle (in the order of not compelling a patient to assume an unnatural posture) for compensation for insufficiency in the rotating angle of the gantry 1. In the examination performed by the inventors of this application, when at lease rotation in the range of from θ=0° to 60° is possible, adjustment of an inclination by means of rotating driving of the patient's bed 8, and position and direction, in which a patient is loaded, make it possible to actually irradiate charged particles on the affected part from a sufficiently multiplicity of angles.

According to the invention, the action of suppressing heightwise variation in a position of the patient's bed 8 from the position at the time of upward irradiation to the position at the time of horizontal irradiation, and the action of reducing the rotary irradiation body in diameter of rotation present a multiplied effect to suppress heightwise variation of the patient's bed (difference of height) to around 1.5 m at maximum provided that positions of respective parts such as eccentric dimension or the like are suitably set. Accordingly, even in a state, in which the patient's bed is in the highest position (the position at the time of upward irradiation and the position at the time of horizontal irradiation), a physician or a technician can perform the irradiation preparing/ascertaining work or the like while standing on a floor without any specific separate device, so that convenience can be considerably improved. Also, since the heightwise position of the patient's bed is suppressed, a patient can be enhanced in safety.

Also, the charged particle irradiation apparatus can be reduced in size as a whole since the diameter of rotation (in other words, a diametrical dimension) and axial dimension of the rotary irradiation body can be reduced. Thereby, there is produced an effect to enable considerably reducing a space, in which a charged particle irradiation apparatus is ordinarily installed having a beam injecting axis corresponding to a center of rotation of a rotating irradiation body, and a dimension (in particular, a heightwise dimension) of an entire building for receiving the charged particle irradiation apparatus and a charged particle generating apparatus.

Further, the construction, in which the above irradiation field forming means is made offset and enlargement of the transport means is correspondingly reduced, makes it possible to make the position of gravity of the entire medical charged particle irradiation apparatus close to the center of rotation as compared with the constitution, in which an irradiation field forming means is diametrically arranged on an outer peripheral side of a patient's bed with a position, in which a patient's bed is arranged, as a position of an axis of rotation of a rotating irradiation body. Thereby, there is produced an effect that, for example, a counter weight required in the above-mentioned construction is made unnecessary, or the necessity therefor is reduced, and lightening of the medical charged particle irradiation apparatus can be achieved correspondingly.

What is claimed is:

1. A charged particle beam irradiating method, comprising the steps of:

arranging a beam transport device for transporting said charged particle beam, an irradiation field forming device for forming an irradiation field for said charged particle beam transported by said beam transport device, a rotating body provided with said beam transport device and said irradiation field forming device and being rotatable about an axis of rotation, said irradiation field forming device being eccentrically arranged to the axis of rotation such that an axis of irradiation thereof passes a position different from the axis of rotation, and a bed for supporting an irradiation target being rotatably suspended from and supported by said irradiation field forming device and being arranged on an opposite side of said beam transport device with respect to a plane which contains the axis of rotation and being substantially perpendicular to the axis of irradiation;

rotating said rotating body such that the axis of irradiation of said irradiation field forming device is matched with a setting irradiation direction of said charged particle beam to said irradiation target;

driving said bed to adjust inclination of said bed; and irradiating said charged particle beam emitted from said irradiation field forming device to said irradiation target.

2. A charged particle beam irradiating method according to claim 1, further comprising the step of detecting inclination of said bed, the inclination of said bed being adjusted by driving said bed based on the detected inclination.

3. A charged particle beam irradiating method according to claim 1, further comprising the step of detecting inclination of said bed, the inclination of said bed being adjusted by rotating said bed based on the detected inclination.

* * * * *